United States Patent [19]

Morita

[11] Patent Number: 5,385,571
[45] Date of Patent: Jan. 31, 1995

[54] LANCET

[75] Inventor: Susumu Morita, Nishinomiya, Japan

[73] Assignee: APLS Co., Ltd., Okayama, Japan

[21] Appl. No.: 13,777

[22] Filed: Feb. 5, 1993

[30] Foreign Application Priority Data

Aug. 28, 1992 [JP] Japan .............................. 4-060676[U]

[51] Int. Cl.6 ............................................ A61B 17/34
[52] U.S. Cl. .................................................. 606/181
[58] Field of Search ............... 606/181, 182, 183, 184, 606/185; 128/637, 770; 628/898

[56] References Cited

U.S. PATENT DOCUMENTS

| | | |
|---|---|---|
| Re. 32,922 | 5/1989 | Levin et al. . |
| 3,358,689 | 12/1967 | Higgins . |
| 4,375,815 | 3/1983 | Burns . |
| 4,379,456 | 4/1983 | Cornell et al. . |
| 4,388,925 | 6/1983 | Burns . |
| 4,414,975 | 11/1983 | Ryder et al. . |
| 4,416,279 | 11/1983 | Lindner et al. . |
| 4,442,836 | 4/1984 | Meinecke et al. . |
| 4,449,529 | 5/1984 | Burns et al. . |
| 4,452,243 | 6/1984 | Leopoldi et al. . |
| 4,462,405 | 7/1984 | Ehrlich et al. . |
| 4,503,856 | 3/1985 | Cornell et al. . |
| 4,514,609 | 4/1985 | Fricke et al. . |
| 4,517,978 | 5/1985 | Levin et al. . |
| 4,535,769 | 8/1985 | Burns . |
| 4,539,988 | 9/1985 | Shirley et al. . |
| 4,545,376 | 10/1985 | Beiter . |
| 4,553,541 | 11/1985 | Burns . |
| 4,577,630 | 3/1986 | Nitzsche et al. . |
| 4,580,564 | 4/1986 | Andersen . |
| 4,580,565 | 4/1986 | Cornell et al. . |
| 4,616,649 | 10/1986 | Burns . |
| 4,624,253 | 11/1986 | Burns . |
| 4,648,408 | 3/1987 | Hutcheson et al. . |
| 4,653,513 | 3/1987 | Dombrowski . |
| 4,658,821 | 4/1987 | Chiodo et al. . |
| 4,676,244 | 6/1987 | Enstrom . |
| 4,677,979 | 7/1987 | Burns . |
| 4,712,548 | 12/1987 | Enstrom . |
| 4,715,374 | 12/1987 | Maggio . |
| 4,735,203 | 4/1988 | Ryder et al. . |
| 4,738,261 | 4/1988 | Enstrom . |
| 4,794,926 | 1/1989 | Munsch et al. . |
| 4,817,603 | 4/1989 | Turner et al. . |
| 4,844,095 | 7/1989 | Chiodo et al. . |
| 4,856,515 | 8/1989 | Turner et al. . |
| 4,858,607 | 8/1989 | Jordan et al. . |
| 4,869,249 | 9/1989 | Crossman et al. . |
| 4,889,117 | 12/1989 | Stevens . |
| 4,892,097 | 1/1990 | Ranalletta et al. . |
| 4,924,879 | 5/1990 | O'Brien . |
| 4,990,154 | 2/1991 | Brown et al. . |
| 4,994,068 | 2/1991 | Hufnagle . |
| 4,995,402 | 2/1991 | Smith et al. . |
| 5,026,388 | 6/1991 | Ingalz . |
| 5,047,044 | 9/1991 | Smith et al. . |
| 5,074,872 | 12/1991 | Brown et al. . |
| 5,100,427 | 3/1992 | Crossman et al. . |
| 5,105,823 | 4/1992 | Blum . |
| 5,133,730 | 7/1992 | Biro et al. . |
| 5,147,375 | 9/1992 | Sullivan et al. . |
| 5,207,699 | 5/1993 | Coe ..................... 606/182 |
| 5,527,561 | 7/1985 | Burns . |

OTHER PUBLICATIONS

Lagana, "Guide to Finger-Pricking Equipment," *Diabetese Self-Management* (R. A. Rapaport Publishing, Inc.), 7, 6–11 (Jul./Aug. 1990).

Primary Examiner—Stephen C. Pellegrino
Assistant Examiner—William W. Lewis
Attorney, Agent, or Firm—Leydig, Voit & Mayer, Ltd.

[57] ABSTRACT

A lancet comprising a lancet body having a needle end protruding from a lancet end, and a needle protector for protecting the protruding needle end before use, the needle protector comprising a hood portion tightly fittable on the lancet end from which the needle end protrudes in such a manner that the hood may be fitted over the lancet end to the needle end to substantially insulate the needle end from the environment after use. The lancet body and the needle protector may be integrally molded, and separated before use to expose the needle end. After use, the hood of the protector may be fitted over the lancet end. Thus, the lancet as a whole can be disposed in a safer manner than the prior art lancets.

16 Claims, 6 Drawing Sheets

LANCET

BACKGROUND OF THE INVENTION

1. Field of the Invention

The present invention relates to a lancet which is a blood collecting needle device, and more particularly to a disposable lancet.

2. Description of Prior Art

Currently, there are many types of electronic blood sugar testers available at the market and easy to use for diagnosis of diabetics. Therefore, the test of blood sugar value is now very widely and often conducted in hospitals and homes, and not only by those who are in charge of diagnosis and treatment but also by the diabetics themselves.

Many people are now concerned more than ever of the diagnosis or prevention of geriatric diseases, and consequently the blood sugar test is now done also for these purposes. The pregnant women in Europe and America take examinations of their blood sugar values at proper intervals during the period of pregnancy.

Depreciation in the selling price of the blood sugar testers has been taking place these years due to the development in technology and the competitive pricing. Such a situation is rapidly increasing the demand and delivery of the blood sugar testers.

The operation for that blood test may usually be executed using a marketed type of finger-pricking device in combination with a disposable lancet attached thereto. A needle protecting cap will be twisted off the lancet so that an acute needle end is exposed, before an internal spring is compressed and locked. Then the device's front end will be pressed against a finger tip from which a blood sample is to be taken, and thereafter the spring will be unlocked to thereby cause the needle end to pierce the finger tip. A small cut is made in this way so that a little amount of blood is sampled from the pricked finger.

Generally, the lancet is replaced with a new one every time when a new blood sample is taken. The used and detached lancet will be discarded with safety using the needle protecting cap which has been twisted off the lancet body. In detail, the cap will be thrust with the used needle end which protrudes from the lancet body (by a distance of about 2.8–3.3. mm and varying between the marketed models) before it is thrown away.

Figure 1:
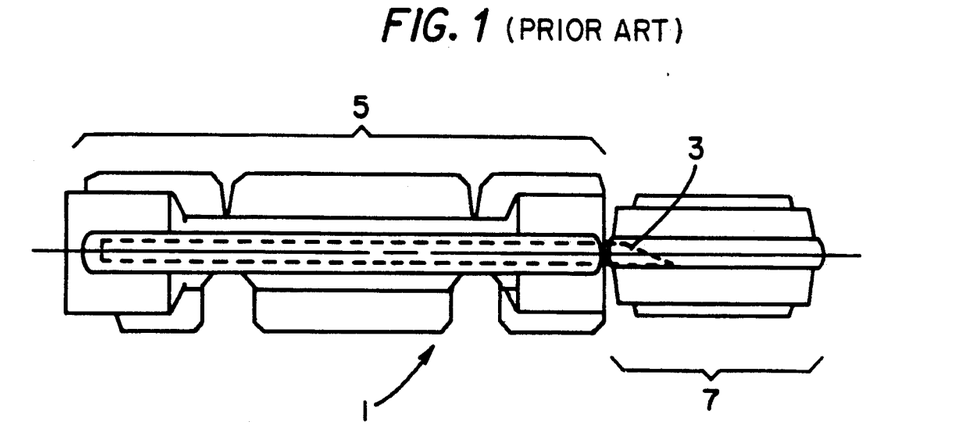
FIG. 1 diagrammatically shows a prior art lancet before use.

Such a prior art lancet 1 is diagrammatically shown in FIG. 1 and comprises a lancet body 5 and a needle protecting cap 7. To use this device, the cap 7 will be twisted off the lancet body 5 at first to expose its needle end 3.

Figure 2:
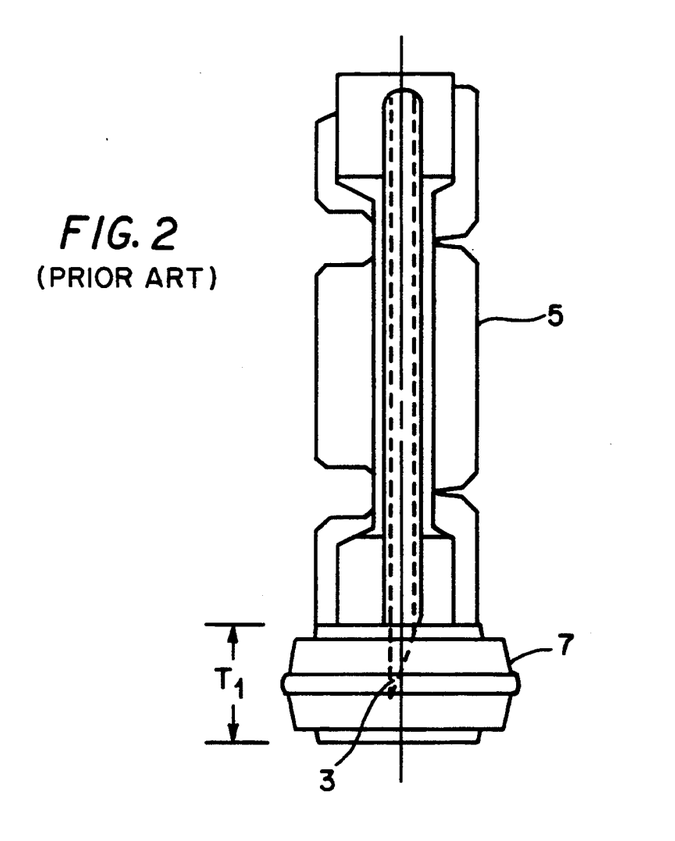
FIG. 2 also diagrammatically shows the prior art lancet after use and in its discarded state.

After use, a side portion of the cap 7 is thrust with the needle end 3 so that this end 3 remains within the cap when and after discarded.

The material forming the protecting cap is usually a linear-molecule low-density polyethylene which is so soft that it can be easily and readily thrust with the needle end.

Twelve typical models of lancets on the market have their needle ends protruding from their lancet bodies by a distance of from about 2.8–3.2 mm. The maximum thickness $T_1$ of the needle protecting caps falls within a range from about 3.8–4.0 mm. Thus, the pointed end of any needle piercing the cap from its one side surface may not jut from its other side surface.

The needle or canula will not usually tend to drop off the cap which it has pierced, since the compressive elasticity of the cap grips the needle.

The force required to pull the needle off the cap which it has pierced depends on the length of needle end exposed out of the lancet body. The longer the needle end, the stronger is the force needed to withdraw it.

The present inventor has carried out a measurement to know the relationship between the exposed length of the needle end (which length is substantially equal to the pierced depth of the cap) and the force needed to withdraw the needle end from the pierced cap. The twelve typical models referred to above were subjected to this measurement (in which five samples were tested for each model). As a result, it was confirmed that the force to withdraw the needle end was 400–500 grams for the shortest needle ends protruding 2.8–2.9 mm, and in contrast with this data, the force of 800–880 grams for the longest needle ends protruding 3.2–3.3 mm.

As was foreseen, the needle end which did not perfectly pierce the cap could be withdrawn with a much weaker pulling force.

This data indicates that, in accordance with the current practice, any needle end used to take a blood sample and pierce the protecting cap can be discarded safely only in a case wherein the protruding length of said needle end is sufficient, and/or the protruding length is fully caught by and fixedly held in the cap, and/or most carefully handled after piercing the cap. If such a condition is satisfied, then the used needle would never be exposed again to the outside and never come into contact with any other person.

In other words, any needle end used to take a blood sample and pierce the protecting cap cannot be discarded safely if the protruding length of said needle end is not sufficient, or the protruding length is not fully caught by and fixedly held in the cap, or not carefully handled after piercing the cap. In such an event, the used needle would possibly be exposed again to the outside and would probably contact other persons.

The hematogenous infection of virus of AIDS (Acquired Immune Deficiency Syndrome) or virus of B-hepatitis is becoming nowadays a serious problem. In the event that a lancet is used to take a blood sample from a carrier of such a disease and thereafter the lancet's needle comes into contact with any other person, this person will catch the carrier's disease.

SUMMARY OF THE INVENTION

An object of the present invention is therefore to meet the social demand for a lancet which can be discarded more safely than the prior art lancets.

This object may be achieved in the present invention by providing a lancet which comprises a lancet body with a needle end protruding from a lancet end; a needle protector for protecting the protruding needle end before use; and the needle protector comprising a hood portion may be tightly fit on the lancet end from which the needle end protrudes, in such a manner that after use the needle end is substantially insulated from the outside.

The words "the needle end . . . substantially insulated" are intended herein to include also a state of the used needle end which is substantially shielded or sealed, or completely closed. However, in the light of the object of the invention, it is sufficient for the words to indicate that the used needle end in the discarded lancet cannot come into contact with a finger tip or other body portion of a person who handles the lancet with usual care. In short, the needle end is herein deemed insulated if it cannot touch the finger tip, even though not perfectly shielded or sealed.

The words "needle end" herein denote a needle portion which has to pierce a human body portion from which a blood sample is to be taken, and the needle portion protrudes from a lancet portion made of a resin and fixedly supporting the needle end. The lancet body is thus composed of the resin portion and the needle end.

The words "needle protector" herein denote a member which insulates and protects the needle end protruding from the lancet body before use. The needle protector is disposed adjacent to the lancet body and capable of being twisted off the lancet body. The needle end is positioned inside the needle protector before use.

The needle protector of the lancet according to the present invention comprises such a hood portion that is may be tightly engaged with the lancet end from which the used needle end will protrude. The hood portion has two regions, one of them receiving the lancet end, while the other region receiving the needle end protruding therefrom. Thus, the hood portion not only receives the lancet end but also insulates the protruding needle end from the outside.

The engagement of the hood portion with the lancet end may be realized with any structure and in any manner insofar as they can surely be brought into a rigid connection to one another. The "rigid connection" means that, once fitted in the hood portion, the lancet end can not be disengaged therefrom in the usual manner of operation in use. Preferably, the rigid connection is stronger and more reliable than the conventional connection of the needle end with the prior art protecting "cap," when handled after use and discarded.

The most preferable structure for ensuring the rigid connection is either "interference fit" or "snap fit." Therefore, the outer periphery of the lancet end as well as the inner periphery of hood portion need be of such a size and shape as enabling the tight fitting of them one on another. In a case wherein both the peripheries of the lancet end and the hood portion are cylindrical, their diameters may differ from one another to such an extent as suitable for the interference fit. In another case wherein one of the peripheries has an annular lug and the other has an annular groove, these lug and groove may be complementary so that they may be snap-fit one on another. The lug and groove need not be continuous around the periphery, but their sections may be arranged at intervals.

BRIEF DESCRIPTION OF THE DRAWINGS

The preferred embodiments will be described below referring to the accompanying drawings, in which.

THE PREFERRED EMBODIMENTS

In an embodiment of the present invention, a lancet comprises a lancet body and a needle protector which is formed with a hood portion, with lancet body having a needle end protruding therefrom. The hood portion has an opening to receive the needle end and a closed bottom opposite to the opening. The closed bottom is of a thickness enough to receive at least partially the needle end which pierces the bottom, and more desirably the thickness is substantially the same or greater than the length of the needle end.

In such a manner as shown in FIGS. 3–6 illustrating the embodiment, the lancet 10 comprises the lancet body 12 and the needle protector 14. The needle end 16 protruding from the lancet body 12 is received in and protected by the needle protector 14, in state shown in FIG. 3 and 4. The protector 14 is connected to the body 12, but is capable of being twisted off the body at a region 18. Accordingly, it is easy for an operator's hand to separate the former from the latter to expose the needle end 16.

Figure 3:
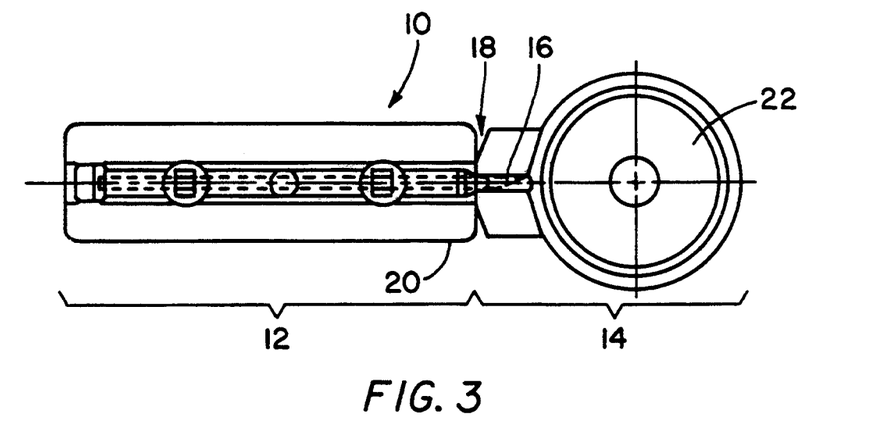
FIG. 3 is plan view of a lancet provided in an embodiment, in its state before use.
Figure 4:
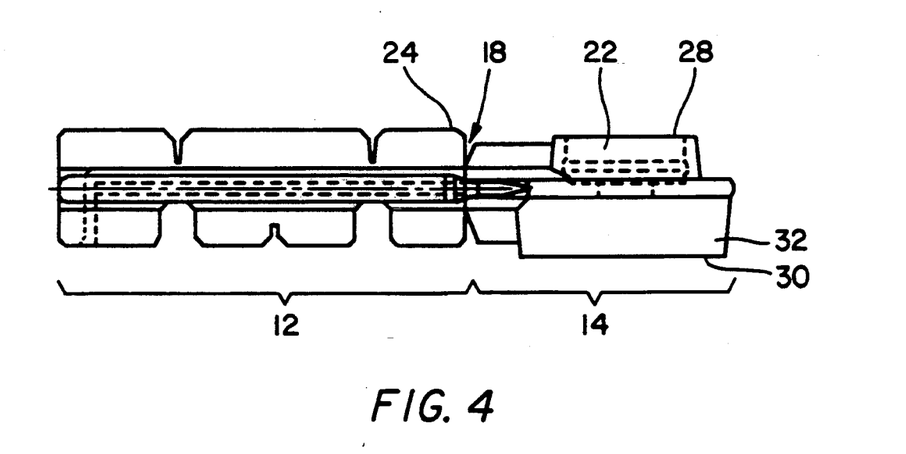
FIG. 4 is a side elevation of the lancet shown in FIG. 3.

The lancet 10 in its unused state shown in FIGS. 3 and 4 will be mounted on an appropriate finger-pricking device. Then the needle protector 14 will be twisted off the lancet body 12 so as to expose the needle end 16 and to render the device ready to use.

Figure 5:
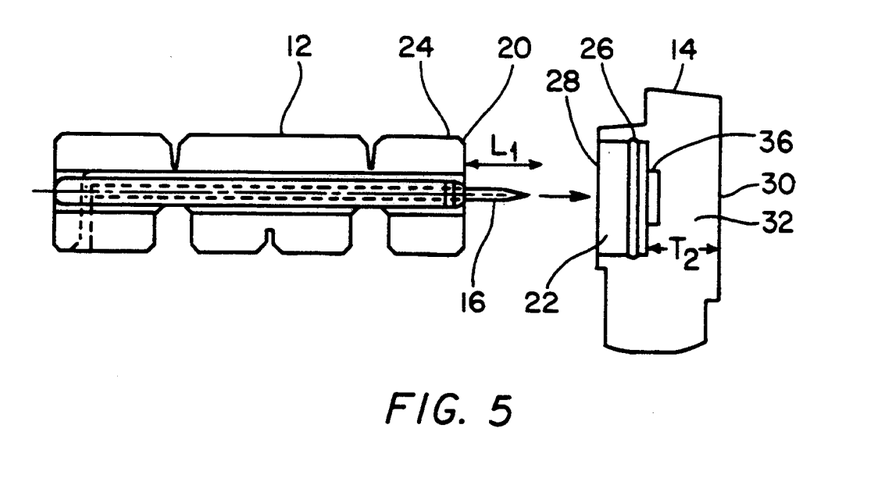
FIG. 5 is also a side elevation illustrating the lancet end of the lancet shown in FIG. 3, in its state before fitted in a hood portion.
Figure 6:
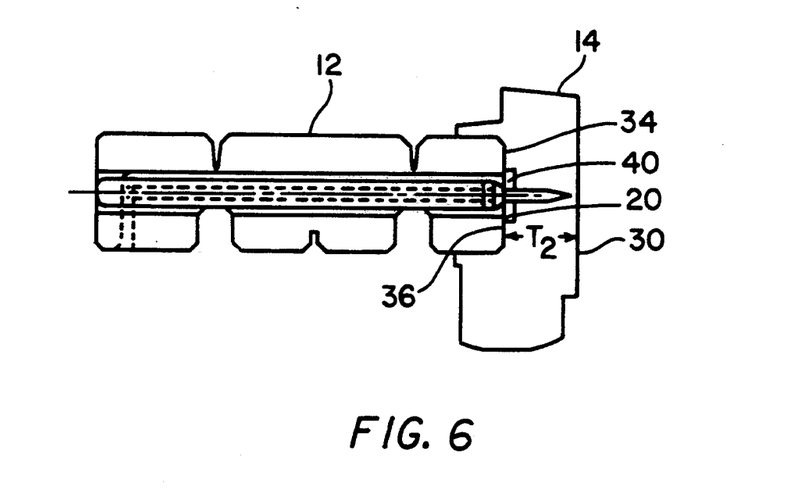
FIG. 6 is another side elevation showing the lancet end fitted in the hood portion.

After use of the device, the lancet end 20 from which the exposed needle end 16 protrudes will be moved towards and fitted in the hood portion 22 of the protector 14, as shown by the arrow in FIG. 5. In this embodiment, the hood portion 22 has an opening 28 to receive the end 20 and a closed bottom 30 opposite to the opening 28. The hood portion 22 is devoid of any pre-bored aperture for the needle end 16, so that the needle end or at least an acute extremity thereof has to pierce a thick wall 32 of the closed bottom 30. Therefore, the thickness of the thick wall 32 (i.e., a distance $T_2$ between an inner surface 34 and an outer surface of the bottom 30, with the inner surface coming into contact with the inserted lancet end) has to be greater than the length $L_1$ of the exposed needle end. In preferable examples, the thickness is usually from 3.8 mm to 5.0 mm. As shown in FIG. 6, the hood portion in this embodiment has a shoulder 36 which prevents a base portion of the needle from contacting the thick wall 30, whereby a gap 40 is formed between the end 20 and the thick wall 30. It is also possible to dispense with the shoulder 36, thereby allowing the needle end to be fully received in the thick wall 30.

The lancet end 20 in this embodiment has lugs 24 which are formed integrally with and disposed along the outer periphery of the end. On the other hand, the hood portion 22 has an annular groove 26 formed integrally with and along the inner periphery of the portion. The lugs 24 can be "snap-fitted" in the groove 26 in a manner shown in FIG. 6. Alternatively, the lugs 24 may be formed on the inner periphery of hood portion, with the annular groove being formed around the outer periphery of the lancet end. In any case, the lugs and the groove must be complementary in their shape and size relative to one another. For example, they may be rectangular or semicircular in cross section. If the groove in the hood portion is rectangular, its width and depth may be 0.8 mm and 0.2 mm, respectively. Correspondingly, the lugs on the lancet end may be four small protrusions which are about 0.8 mm wide and about 0.2 mm wide.

In a further embodiment of the invention, the hood portion of the needle protector is formed with a bore which penetrates the bottom of the opening receiving the lancet end. The bore has an open end opposite to the opening, and the bore and its open end must have such a length and diameter and be of such a shape as adapted to insulate the needle end.

A preferable structure in the further embodiment is shown in FIGS. 7–10, and similarly to the already described embodiment, the lancet 10 also comprises the lancet body 12 and the needle protector 14. The needle end 16 protrudes from the body 12 and is positioned in and protected by the protector 14. The protector 14 is connected to the body 12, but is capable of being twisted off the body at a region 18. Accordingly, it is also easy for the operator's hand to separate the former from the latter to expose the needle end 16.

Figure 7:
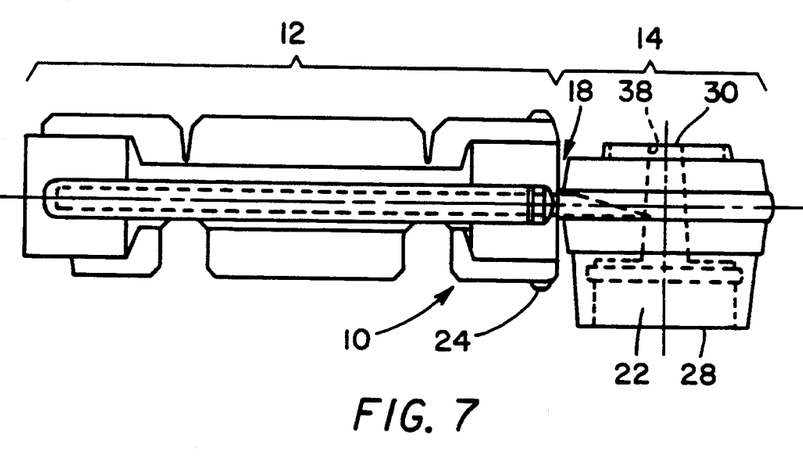
FIG. 7 is a side elevation showing a lancet provided in a further embodiment, in its state before use.

The lancet 10 in its unused state shown in FIG. 7 will be mounted also on an appropriate finger-pricking device. Then the needle protector 14 will be twisted off the lancet body 12 so as to expose the needle end 16 and to render the device ready to use.

Figure 8:
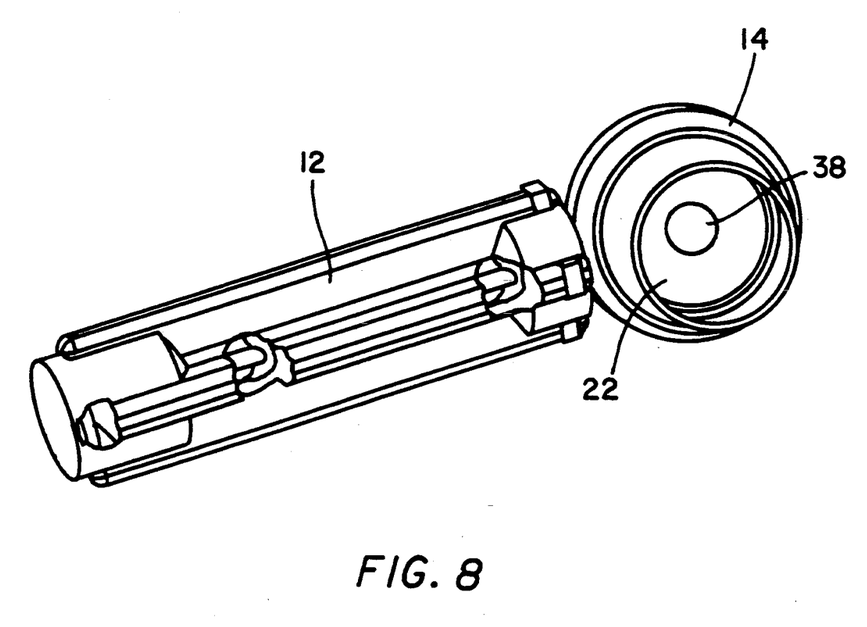
FIG. 8 is a bottom perspective view the lancet shown in FIG. 7.
Figure 9:
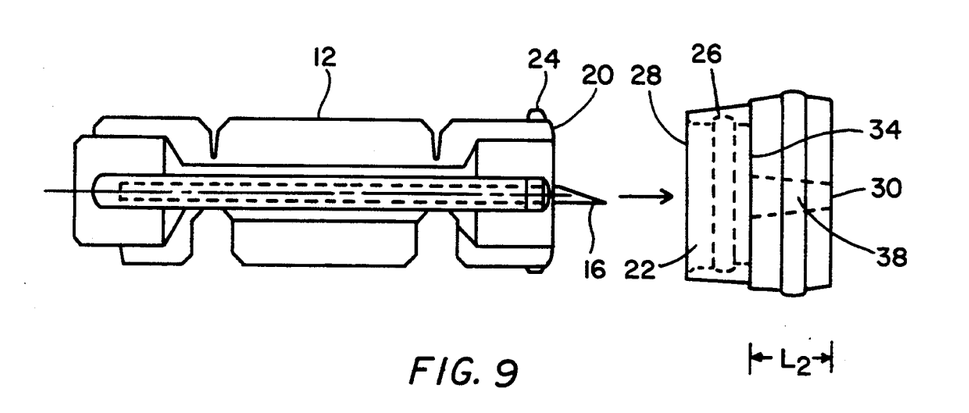
FIG. 9 is also a side elevation illustrating the Lancet end of the lancet shown in FIG. 7, in its state before fitted in a hood portion.
Figure 10:
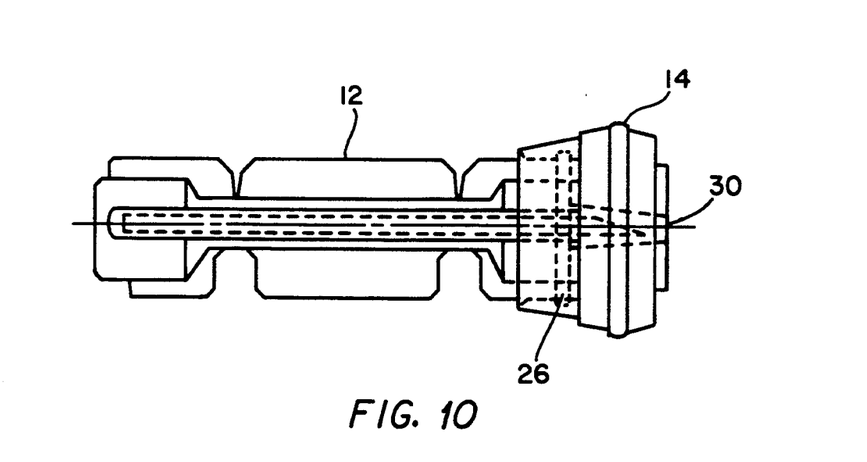
FIG. 10 is another side elevation showing the lancet end fitted in the hood portion.

After use of the device, the lancet end 20 from which the exposed needle end 16 protrudes will be moved towards and fitted in the hood portion 22 of the protector 14, as shown by the arrow in FIG. 9. In this embodiment, the hood portion 22 has an opening 28 to receive the end 20 and a bottom. This bottom has an open end 30 opposite to the opening 28, and a bore 38 is formed between the open end 30 and the opening 28. The length and shape of the bore 38 are designed such that the operator's finger cannot enter the bore, or cannot contact the needle end even if it had entered the bore. The shape of bore at the open end 30 may be circular, rectangular, polygonal or the like, and the dimension in an equivalent diameter "D" of the bore at the open end may be preferably from about 1.0 mm–4.0 mm, and more preferably about 2.0 mm. Because it may occur that a finger tip portion is forced into the bore from through the open end 30 even though the finger itself could not enter it, the bore preferably has an appropriate length $L_2$ of about 3.5–5.0 mm, and more preferably 3.8–4.0 mm, as shown in FIG. 9. As shown in FIG. 8, the hood portion is not formed with any shoulder 36 which produces the gap 40 around the root or base portion of the needle end, as in the preceding embodiment. Thus, the needle end is fully received in the bore 38.

The lancet end 20 in this embodiment also has lugs 24 formed on the outer periphery of the end. On the other hand, the hood portion 22 has an annular groove 26 formed integrally with and along the inner periphery of the portion. The lugs 24 can be "snap-fitted" in the groove 26 in a manner shown in FIG. 10. Alternatively, the lugs 24 and groove 26 may be dispensed with, and, instead, the lancet end and the hood portion may be of such a shape and size as enabling their "interference fit."

In a still further embodiment of the invention, the hood portion of the needle protector is formed with an elongate recess which extends outwardly from the bottom of the opening receiving the lancet end. However, the elongate recess terminates short of the bottom's outer surface opposite to the opening. The needle end is received in and insulated from the outside by the elongate recess.

Figure 11:
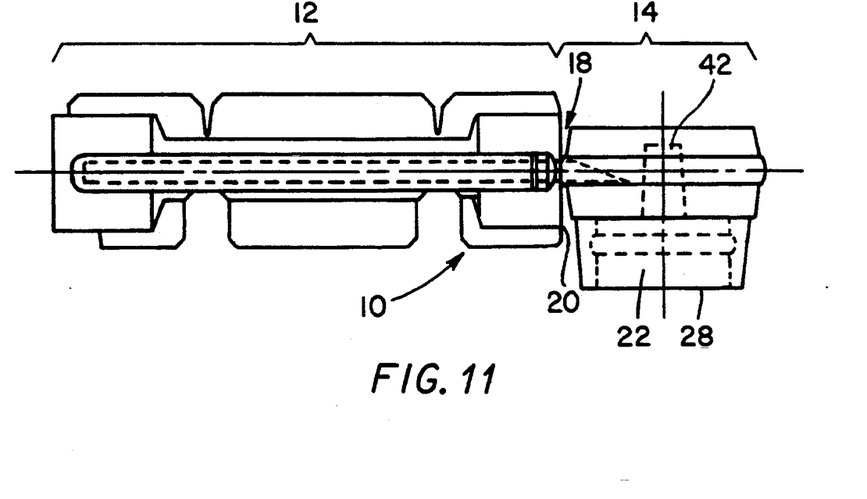
FIG. 11 is a side elevation showing a lancet provided in a still further embodiment, in its state before use.

As will be seen clearly from FIG. 11, the lancet in the still further embodiment does not differ from that in the further embodiment shown in FIGS. 7–10, except for the elongate recess 42 opposite to the opening 28 and the interference fit of the lancet end in the hood portion.

Figure 12:
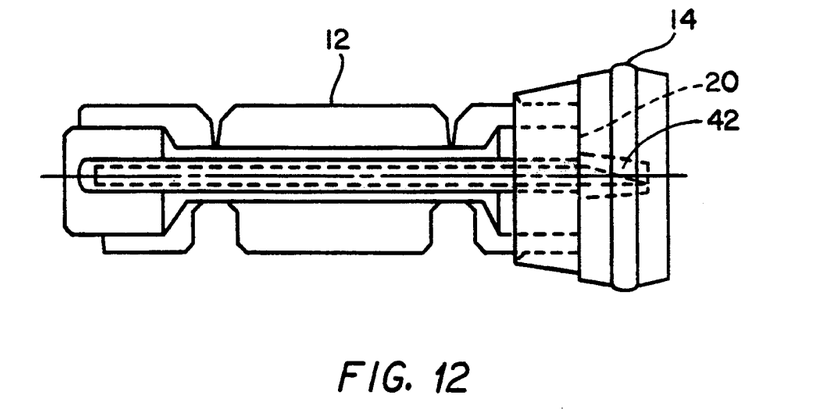
FIG. 12 is also a side elevation illustrating the lancet end of the lancet shown in FIG. 11, in its state after fitted in a hood portion.
Figure 13:
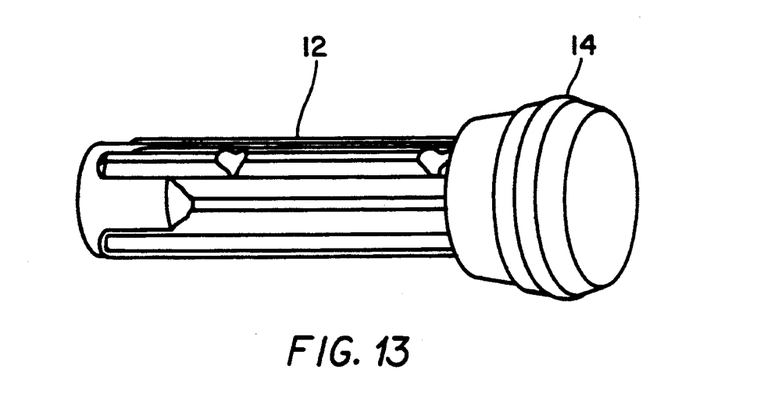
FIG. 13 is a perspective view corresponding to FIG. 12.

The depth and shape of the elongate recess 42 are not restricted to those shown in the drawings but may be modified in any manner, provided that at least the acute extremity of the needle end can be received. Usually, the elongate recess is circular in cross section having a diameter substantially equal to that of the needle end, though it may be of a rectangular, polygonal or the like cross section. Likewise, the depth of the elongate recess is modifiable on the condition that the needle end is entirely received or at least its distal portion is received (as shown in FIG. 12) in said recess.

The lancet end 20 in this embodiment is fitted close in hood portion 22, by the so-called "interference fit" or "stationary fit" mechanism. Therefore, neither lugs nor groove are formed on these members which engage tightly with one another.

The above embodiments are some highly desirable modes, but the present invention is not necessarily limited to those embodiments. The invention may include any other embodiments in which the lancet end is hardly disengageable from the hood portion of the needle protector and the needle end is substantially insulated from the outside.

Among the three embodiments given above, those which are shown in FIG. 7 or FIG. 11 can be produced more easily and are more advantageous than that shown in FIG. 3.

It is an important feature in the present invention that the hood portion 22 has a stopper surface (e.g., the portion 34 in the drawings) which contacts and supports the lancet end inserted through the opening 28 located opposite to said surface. Each of the illustrated embodiments comprises the stopper surface, and in FIG. 3 the thick wall 32 will function as such a stopper surface if the shoulder is dispensed with.

Any appropriate materials such as those which have been used to make the prior art lancets may be employed herein to form the lancet in accordance with the present invention. A stainless steel needle having a diameter of 0.65 mm may be employed herein to be supported and protected by the needle protector, which in turn may be formed with a proper plastics such as a linear-molecular low-density polyethylene, polypropylene or low-density polyethylene.

In a case wherein the plastic needle protector is formed integrally with the needle, the lancet body can also be produced integrally with the needle protector. Alternately, the lancet body and the protector may be prepared separately and combined thereafter by an appropriate means. For the purpose of shielding or protecting the unused needle end, the former case is preferable.

In use, the operator who will have taken a blood sample may put the needle protector on a table in such a state that the opening of the hood portion faces upwards. The lancet body will be positioned such that its end faces downwards, and then be pressed against the protector, thus causing its opening to receive the lancet end.

Since both the lancet body and the protector are made of a considerably soft plastics, such as linear-molecular low-density polyethylene, the lancet end will expand and advance into the hood portion of the protector, without any remarkable difficulty, until the four lugs on the lancet end gently click into the groove in the hood portion. At the same time, said end contacts the stopper surface and the lancet body is stopped and secured stationary in this place.

In an example of the described embodiment(s), the outer radial ends of four lugs on the lancet end are on a single circumcircle whose diameter is greater than the inner diameter of the hood portion of the needle protector by about 0.4 mm (corresponding to a difference of 0.2 mm in radius). Once the lugs fit in the groove, they can hardly be put out of place. In another example of the described embodiment(s), the "interference fit" is substituted for the "snap fit" mechanism. This substitution, however, does not impair the rigid connection of the hood portion to the lancet end.

The needle end, which pierces the thick wall or is accommodated in the bore or the elongate recess in the embodiments, is thus surely insulated from the outside.

In the preferable examples described above, the end surface of the lancet end will contact the bottom surface of the hood portion when the lancet body is pressed into the protector. This contact of the surfaces stops the lancet body so that, even if an excessively strong force is applied, it cannot advance ahead beyond the predetermined position where the "snap fit" or "interference fit" occurs. Thus, the lancet end will always take said position regardless of the strength of applied force.

In a case wherein the "snap fit" mechanism is employed, the force urging the lancet body will be lost suddenly when the lugs snap in the groove. This gives a signal to the operator so that he or she can easily sense the perfect engagement the mating members, thus avoiding any imperfect coupling thereof.

In a case wherein the outer surface 30 of the bottom of needle protector lies in parallel with the opening 28 thereof, as shown in the drawings, the protector can rest stably on a table in such a state that the surface 30 is in contact with the table, with the opening thereby facing upwards. Consequently, the operator can press down the lancet body towards the protector on the table, without any danger of erroneously injuring his or her finger with the used needle end.

After the lancet end is received in and fixedly engaged with the hood portion, the protector not only insulates the needle end from the outside but also covers the lancet end. Although a small amount of blood is likely to be left sticking to the needle end after the blood sampling, this lancet is much safer than the prior art ones.

EXAMPLE

A lancet was designed which was of such a structure as shown in FIG. 11 illustrating one embodiment of the invention, and a mold was manufactured to have the following designed dimensions. The portion giving the lancet body had a diameter of 6.5 mm, and a length of 22.9 mm; each of the portions giving the lugs had a height of 0.2 mm, a width of 0.8 mm and a length of 1 mm; the portion giving the hood portion of the protector had an inner diameter of 6.5 mm and a depth 2.95 mm; the portion giving the elongate recess receiving the needle end had an inner diameter of 2 mm and a depth of 3.5 mm; and the protruding length of the needle end was 3.15 mm.

The mold was set in an injection molding machine of the pressing capacity of 20 tons, made by the NISSEI RESIN INDUSTRIES CO., LTD. Needles made of SUS304 stainless steel and having an outer diameter of 0.65 mm and a length of 25.4 mm were inserted in respective cavities of the mold. An amount of "REXLON" (a trademark of a linear low-density polyethylene made by NIHON PETROCHEMICALS CO., LTD.) was injected into the cavities to form one hundred sets of the lancets of the present invention. Each lancet comprised the lancet body integral with the needle protector. The molding process was smooth as in the case of the prior art lancets.

Fifty lancets were selected in a random manner from the one hundred lancets thus molded. Their needle protectors were twisted off the respective lancet bodies and placed on a table so that their openings faced upwards. The lancet ends from which the needle ends protruded were positioned downwards to face the respective hood portions of said protectors, and then forced into the hood portions. Due to curved guiding edges having a radius of 0.4–0.5 mm and formed around an end surface of each lancet body and around an entrance of each hood portion, the lancet bodies could be inserted very smoothly into the respective hood portions. The lugs on each lancet body were clicked into the groove in each hood portion, thereby affording the neat and sure engagement of the former with the latter.

It was observed that, with each lancet body being pressed into the hood portion of each protector, the needle end entered automatically the elongate recess having the inner diameter of 2 mm and the depth of 3.5 mm.

The fifty lancet bodies which had been connected in this manner to the protectors were then successively mounted on a tensile tester "9250B" made by the AIKO ENGINEERING CO., LTD. Each needle protector was clamped and fixed in place, while the lancet body was pulled away from the protector so as to measure the force (which corresponded to the strength of "snap fit") needed to separate the latter from the former.

A maximum, minimum and average forces for separation were 1.39 Kg, 0.98 Kg and 1.12 Kg, respectively. As referred to hereinbefore, the maximum and minimum separation forces were respectively 880 grams and 400 grams for the twelve types of the marketed prior art lancets. Thus, the fact that the snap fitting of the protector on the lancet body in the invention is effective to the rigid connection between them was clearly confirmed.

Each lancet end with the needle end protruding therefrom was put into the hood portion a distance of about 26 mm so as to be entirely shielded therein. This state of the structure thus proved safer than the prior art lancets each comprising the needle end which merely pierces the protecting cap and each also comprising the lancet end which remains exposed.

The lancets in the present invention can be produced with a mold which is not of any sophisticated or complicated structure. The molded lancets can be easily discharged from the mold, and the insertion of the needles in the cavities of the mold can be done in the same manner as the prior art. Therefore, it is feasible to produce and supply the lancets of the invention at a relatively low price, in a stable manner and on a large scale, similar to the prior art lancets.

The present invention can be applied to any type of lancets whose needle ends are of a varied length protruding from their lancet ends.

All the finger-pricking devices which are currently on the market for use with the prior art lancets are also applicable to the lancets of the invention.

What is claimed is:

1. A lancet comprising:
   a needle end;
   a lancet body, the needle end being molded in the lancet body and protruding from a lancet end of the lancet body;
   a separable needle protector unitarily formed with said lancet body and needle end such that the needle end is embedded in said protector to protect the needle end before use; and
   the needle protector comprising a hood portion having an opening and being tightly fittable to the lancet end from which the needle end protrudes, the hood portion having a flat contact base substantially larger than and opposite the opening, the hood portion thereby being substantially free-standing with the opening upwardly oriented in such a manner that the lancet end, after use, may be tightly engaged by interference or snap fit into said opening to substantially insulate the needle end from the environment by inserting the lancet end substantially downwardly into the opening thereby to surround the lancet end of the lancet body with the hood portion, so as to be separable only upon application of a force in excess of about 1 Kg.

2. The lancet as defined in claim 1, wherein the lancet end is interference-fitted in the hood portion of the needle protector.

3. The lancet as defined in claim 2 wherein the hood portion has at its one end an opening for receiving the lancet end, and at its other end a closed bottom comprising a thick wall which is pierced by at least a portion of the protruding needle end.

4. The lancet as defined in claim 2 wherein the hood portion has at its one end an opening for receiving the lancet end, and at its other end a bottom through which a bore is formed with a further opening, and wherein each of the bore and the further opening is of such a length, diameter and shape as to insulate the needle end from the outside.

5. The lancet as defined in claim 2 wherein the hood portion has at its one end an opening for receiving the lancet end, and at its other end a bottom having an elongate recess which extends towards but short of the other end in such a manner as to insulate the needle end from the outside.

6. The lancet as defined in claim 1, wherein the lancet end is snap-fitted in the hood portion of the needle protector.

7. The lancet as defined in claim 6 wherein the hood portion has at its one end an opening for receiving the lancet end, and at its other end a closed bottom comprising a thick wall which is pierced by at least a portion of the protruding needle end.

8. The lancet as defined in claim 6 wherein the hood portion has at its one end an opening for receiving the lancet end, and at its other end a bottom through which a bore is formed with a further opening, and wherein each of the bore and the further opening is of such a length, diameter and shape as to insulate the needle end from the outside.

9. The lancet as defined in claim 6 wherein the hood portion has at its one end an opening for receiving the lancet end, and at its other end a bottom having an elongate recess which extends towards but short of the other end in such a manner as to insulate the needle end from the outside.

10. The lancet as defined in claim 1 wherein the hood portion has at its one end an opening for receiving the lancet end, and at its other end a closed bottom comprising a thick wall which is pierced by at least a portion of the protruding needle end.

11. The lancet as defined in claim 1 wherein the hood portion has at its one end an opening for receiving the lancet end, and also has at its other end a bottom through which a bore is formed with a further opening, and wherein each of the bore and the further opening is of such a length, diameter and shape as to insulate the needle end from the outside.

12. The lancet as defined in claim 1 wherein the hood portion has at its one end an opening for receiving the lancet end, and at its other end a bottom having an elongate recess which extends towards but short of the other end in such a manner as to insulate the needle end from the outside.

13. The lancet as defined in claim 1, wherein the lancet body and the needle protector comprise molded polymeric material.

14. The lancet as defined in claim 1, wherein the lancet is unitarily molded in a single two part mold having no movable cores.

15. A method of insulating from the environment the needle end of a lancet body unitarily molded with a needle protector in which the needle end is embedded during molding, comprising the steps of:
   (a) separating the needle end from an integrally molded hood portion of the needle protector;
   (b) placing a flat contact base of the needle protector on a supporting surface such that the needle protector is free-standing with an opening in the needle protector upwardly oriented;
   (c) and pressing the lancet body and needle end downwardly into the opening in the free-standing needle protector, positively but releasably engaging the lancet body with the opening by interference fit or snap fit whereby the needle end is substantially insulated from the environment, the lancet body and needle protector being separable only upon application of a substantial force in excess of about 1 kg.

16. In a method of insulating the needle end of a lancet body unitarily molded with a needle protector in which the needle end is embedded during molding, the steps of:
   (a) before use, separating the needle end from a molded hood portion of said needle protector, (b) after use of the needle, placing a flat contact base of the needle protector on a surface such that the needle protector is free standing with an opening in the needle protector upwardly oriented, and (c) inserting the lancet body and needle end downwardly into the opening, thereby tightly engaging the lancet body releasably into said opening by interference fit or snap fit to insulate the used needle end, so that the lancet body and needle protector are separable only upon application of a substantial force in excess of about 1 kg.

* * * * *